United States Patent [19]

Sakuta et al.

[11] Patent Number: 4,970,252
[45] Date of Patent: Nov. 13, 1990

[54] OILY PASTE COMPOSITION

[75] Inventors: Koji Sakuta; Satoshi Kuwata, both of Annaka, Japan

[73] Assignee: Shin-Etsu Chemical Company, Ltd., Tokyo, Japan

[21] Appl. No.: 480,004

[22] Filed: Feb. 14, 1990

[30] Foreign Application Priority Data

Feb. 15, 1989 [JP] Japan ................................. 1-35836

[51] Int. Cl.$^5$ .............................. C08K 5/54; C08K 5/01
[52] U.S. Cl. ..................................... 524/268; 428/78; 524/491; 524/500; 524/588; 525/477
[58] Field of Search ............... 524/268, 588, 500, 491; 525/477; 424/78

[56] References Cited

U.S. PATENT DOCUMENTS

| | | | |
|---|---|---|---|
| 2,771,422 | 11/1956 | Browning et al. | 524/268 |
| 2,804,440 | 8/1957 | Brown | 524/268 |
| 4,163,673 | 8/1979 | Dechert | 524/588 |
| 4,624,899 | 11/1986 | Macaigne et al. | 524/268 |
| 4,824,891 | 4/1989 | Laurent et al. | 524/491 |

FOREIGN PATENT DOCUMENTS

| | | |
|---|---|---|
| 569776 | 1/1959 | Canada. |
| 56-95663 | 8/1981 | Japan. |
| 62-84166 | 4/1987 | Japan. |

*Primary Examiner*—Veronica P. Hoke
*Attorney, Agent, or Firm*—Oblon, Spivak, McClelland, Maier & Neustadt

[57] ABSTRACT

An oily paste composition comprising, as essential components, (I) a polymerization product obtained by addition polymerization of (A) an organohydrogenpolysiloxane containing in its molecule not less than 1.5 silicon-bonded hydrogen atoms on average and (B) an organopolysiloxane containing in its molecule not less than 1.5 silicon-bonded aliphatic unsaturated groups on average, and (II) a saturated hydrocarbon oil.

The present composition is smooth to touch, free from stickiness, and excellent in transparency. It is useful for, for example, cosmetic or medical purpose.

8 Claims, No Drawings

OILY PASTE COMPOSITION

BACKGROUND OF THE INVENTION

1. Field of the Invention

This invention relates to an oily paste composition mainly composed of a saturated hydrocarbon oil, having a good transparency and being free from stickiness. It also relates to a cosmetic material and a polishing material which contains the composition.

2. Description of the Prior Art

Pasty compositions comprising a saturated hydrocarbon oil have been hitherto used in various industrial fields. In preparing such oily paste compositions, a thickening agent is required to be mixed into the saturated hydrocarbon oil.

The thickening agents used for such a purpose include, for example, organic ones such as dextrin fatty acid esters, sucrose fatty acid esters and D-sorbitol/benzaldehyde condensates, and inorganic ones such as organically-modified minerals. However, the oily paste compositions containing the organic thickening agents have a sticky feel and hence involve the problem of poorness in feeling when used. The compositions containing the inorganic thickening agents cause a loss of transparency. and have a poor smoothness, giving a rough feeling in use; moreover, they undergo changes with time to cause separation of the saturated hydrocarbon oil, bringing about the problem that they lack storability.

SUMMARY OF THE INVENTION

Accordingly, an object of this invention is to provide a novel oily paste composition having eliminated the above prior art problems that have occurred in the oily paste compositions mainly composed of the saturated hydrocarbon oil.

The present inventors found that an oily paste composition, which achieves the above object, can be obtained from (i) a polymerization product comprising a polymer having three-dimensional structure, obtained under specific conditions as described later, and (ii) a saturated hydrocarbon oil. They thus accomplished this invention.

The oily paste composition of this invention comprises:

(I) 100 parts by weight of a polymerization product obtained by addition polymerization of an organohydrogenpolysiloxane of (A) given below and an organopolysiloxane of (B) given below in the presence of at least one member selected from the group consisting of a saturated hydrocarbon oil of (C) given below and a low-viscosity silicone oil of (D) given below; and (II) from 10 to 1,000 parts by weight of a saturated hydrocarbon oil of (C) given below.

(A): An organohydrogenpolysiloxane containing in its molecule not less than 1.6 silicon-bonded hydrogen atoms on average.

(B): An organopolysiloxane containing in its molecule not less than 1.5 silicon-bonded aliphatic unsaturated groups on average.

(C) A saturated hydrocarbon oil with a boiling temperature range of from 70 to 360° C.

(D): A low-viscosity silicone oil with a viscosity of not more than 100 cSt at 25° C.

DETAILED DESCRIPTION OF THE INVENTION

(I) Polymerization Product

The component (I) polymerization product, which is an essential component, is obtained by addition polymerization of the reactive organopolysiloxanes of the above (A) and (B) in the presence of the saturated hydrocarbon oil of the above (C) and/or the low-viscosity silicone oil of the above (D). In other words, the polymerization product is comprised of a polymer having three-dimensional crosslinked structure and the oil of the above (C) or (D) or a mixed oil of the both incorporated in the inside of the polymer.

(A) Organohydrogenpolysiloxane

The organohydrogenpolysiloxane of (A) used in preparing this polymerization product contains in its molecule not less than 1.5, and preferably 2 to 5, silicon-bonded hydrogen atoms (Si—H bonds) on average. It is composed of some or all of an $HSiO_5$ unit, an $RSiO_{1.5}$ unit, an $RHSiO$ unit, an $R_2SiO$ unit, an $R_2HSiO_{0.5}$ unit, an $R_3SiO_{0.5}$ unit and the like.

This organohydrogenpolysiloxane may be linear, branched, or cyclic, but may preferably be linear so that the synthesis reaction to obtain the polymerization product described later can smoothly proceed.

The silicon-bonded hydrogen atoms in the molecule of the above organohydrogenpolysiloxane may preferably be in an amount of from 0.5 to 20 mol %, based on the total of the silicon-bonded hydrogen atoms and organic groups The organic group contained in the organohydrogenpolysiloxane is the group represented by R in the units described above. It is exemplified by substituted or unsubstituted monovalent hydrocarbon groups except unsaturated aliphatic groups. It specifically includes hydrocarbon groups, e.g., an alkyl group such as methyl, ethyl, propyl or butyl; an aryl group such as phenyl or tolyl; a cycloalkyl group such as cyclohexyl: and substituted hydrocarbon groups in which one or more hydrogen atoms possessed by the above hydrocarbon group have been substituted with a halogen atom such as chlorine, bromine or fluorine, a cyano group, etc. as exemplified by a gamma-trifluoropropyl group and a chloromethyl group.

The above group R may preferably be the methyl group. In particular, preferably used is an organohydrogenpolysiloxane in which not less than 50 mol % of R's is comprised of the methyl group.

Typical examples of the above organohydrogenpolysiloxane include a compound represented by the formula:

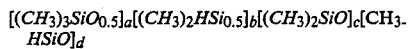

$[(CH_3)_3SiO_{0.5}]_a[(CH_3)_2HSiO_{0.5}]_b[(CH_3)_2SiO]_c[CH_3HSiO]_d$ wherein a and b are each an integer of 0, 1 or 2 that satisfies the relationship of $a+b=2$; c is an integer of from 0 to 500; and d is an integer of from 0 to 50.

(B) Organopolysiloxane

The organopolysiloxane of (B) contains in its molecule not less than 1.5, and preferably from 2 to 5, silicon-bonded aliphatic unsaturated groups on average. This organopolysiloxane includes those composed of some or all of an $(CH_2=CH)SiO_{1.5}$ unit, an $RSiO_5$ unit, an $R(CH_2=CH)SiO$ unit, an $R_2SiO$ unit, an $R_2(CH_2=CH)SiO_{0.5}$ unit or an $R_3SiO_{0.5}$ unit (wherein R is as defined above).

The molecular structure of this organopolysiloxane may be linear, branched, or cyclic, but may preferably be linear so that the synthesis reaction to obtain the polymerization product can smoothly proceed.

The aliphatic unsaturated group contained in the organopolysiloxane includes, for example, a vinyl group and an allyl group. In general, it may preferably be a vinyl group. The aliphatic unsaturated groups may preferably be contained in an amount of from 0.5 to 20 mol % of the silicon-bonded organic groups. The organic group other than the aliphatic unsaturated group may preferably include, for example, the methyl group. In particular, not less than 50 mol % of other organic groups may preferably be comprised of methyl groups.

Typical examples of the above organopolysiloxane of (B) include a methylvinylpolysiloxane represented by the formula:

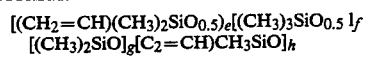
$[(CH_3)_2SiO]_g[C_2=CH)CH_3SiO]_h$ wherein e and f are each an integer of 0, 1 or 2 that satisfies the relationship of $e+f=2$; g is an integer of from 0 to 500; and h is an integer of from 0 to 50. These may be in the form of a mixture.

As described above, in both of the (A) organohydrogenpolysiloxane and the (B) organopolysiloxane, the number of the corresponding reactive group, i.e. the silicon-bonded hydrogen atom or aliphatic unsaturated group, in the molecule is required to be not less than 1.5 on average. The number otherwise less than 1.5 for either of them makes it difficult to form the three-dimensional crosslinked structure in the polymer obtained by addition polymerization, causing insufficiency in the thickening properties of the resulting polymerization product (I) and also causing insufficiency in the thickening effect to the intended oily paste composition.

As previously described, these reactive groups may preferably be contained in an amount ranging from 0.5 to 20 mol % of the silicon-bonded hydrogen atoms and organic groups in the respective polysiloxanes (A) and (B). The content more than 20 mol % may make the resulting polymer too hard for the saturated hydrocarbon oil of (C), the low-viscosity silicone oil of (D) or the mixed oil of the both to be readily incorporated into the three-dimensional crosslinked structure. As a result, the separation of the above oil component (C) and/or (D) may be easily caused. Thus, the resulting oily paste composition has poor storability. On the other hand, a content less than 0.5 mol %, of the reactive groups makes insufficient the formation of the three-dimensional crosslinked structure. thereby increasing the solubility of the component (II) polymerization product to the saturated hydrocarbon oil of the component (II). Thus, it follows that the resulting oily paste composition does not have sufficient viscosity.

(C) Saturated Hydrocarbon Oil

The saturated hydrocarbon oil of (C) used for the preparation of the component (I) polymerization product includes, for example, ligroin, mineral spirit, kerosene, and isoparaffins. There are no limitations as to whether they are in the form of a single matter or a mixture, so long as they have a boiling temperature range of from 70 to 360° C., and preferably from 90 to 270 C. It, however, is preferred to use isoparaffins because of its less skin irritation or less possibility of affecting the surface to be coated. The isoparaffin may include, for example, Isopar C, Isopar E, Isopar G, Isopar H, Isopar L, and Isopar M (trade names for products of Exxson Chemical Japan Ltd.). Isozole 200, Isozole 300, and Isozole 400 (trade names for products of Nippon Petrochemicals Co., Ltd.), lp Solvent 1016, lp Solvent 1620, lp Solvent 2028, and lp Solvent 2835 (trade names for products of Idemitsu Petrochemical Co., Ltd.), and Marukazole R (a trade name for a product& of Maruzen Petrochemical Co., Ltd.).

Saturated hydrocarbon oils having a boiling temperature lower than 70° C. have particularly so strong a skin irritation that the problem of skin chapping may occur. Those having a boiling temperature higher than 360° C. have so low a volatility that oil contents may remain to bring about a sticky feel. Thus, these are not suited to this invention.

(D) Low-viscosity Silicone Oil

As the low-viscosity silicone oil of (D) used in this invention, any silicone oil can be used without any particular limitations so long as it has a viscosity of not more than 100 cSt at 25° C., and preferably not more than 50 cSt. The viscosity higher than 100 cSt may bring about a sticky feel in the resulting oily taste composition.

The low-viscosity silicone oil specifically includes linear or branched siloxanes with a low degree of polymerization, such as methylpolysiloxane, methylphenylpolysiloxane, ethylpolysiloxane, ethylmethylpolysiloxane and ethylphenylpolysiloxane, and cyclic ones such as octamethylcyclotetrasiloxane and decamethylcyclopentasiloxane. One or more of them can be used under appropriate selection as required. Particularly preferred are methylpolysiloxanes, methylphenylpolysiloxanes, and cyclic dimethylpolysiloxanes.

Preparation of Polymerization Product (I)

The component (I) polymerization product in the oily paste composition of this invention is prepared by subjecting the organohydrogenpolysiloxane of (A) and the organopolysiloxane of (B) to addition polymerization in the presence of at least one member selected from the saturated hydrocarbon oil of (C) and the low-viscosity silicone oil of (D).

The organohydrogenpolysiloxane of (A) and organopolysiloxane of (B) may be used in the addition polymerization preferably in an amount such that the molar ratio of the silicon-bonded hydrogen atoms possessed by (A) to the silicon-bonded aliphatic unsaturated groups possessed by (B) ranges from 1/3 and 3/1 and particularly preferably from 1/2 to 2/1. The ratio otherwise either excessively large or excessively small may cause unreacted components (i.e., the silicon-bonded hydrogen atoms or silicon-bonded aliphatic unsaturated groups) to remain in the resulting polymerization product, resulting in impairment of storability of the end product oily paste composition.

silicone oil of (D) or the mixed oil of the both used an amount of from 10 to 1,000 parts by weight, and preferably from 20 to 500 parts by weight. based on 100 parts by weight of the total weight of the (A) organohydrogenpolysiloxane and (B) organopolysiloxane. This is because the amount less than 10 parts by weight makes small the effect of using it together, resulting in a lowering of the thickening properties of the resulting polymerization product. It also follows that the resulting oily paste composition tends to lose its transparency then the component (I) polymerization product is kneaded with the component (II) saturated hydrocarbon oil under application of shearing force. On the other hand, the amount more than 1.000 parts by weight may result in a lowering of the reaction rate between the organohydrogenpolysiloxane of (A) and organopolysiloxane of (B), making it impossible to obtain a polymerization product with sufficient thickening properties.

Because of the presence of the saturated hydrocarbon oil of (C), the low-viscosity silicone oil of (D) or the mixed oil of the both in the above reaction, the desired oily paste composition comprising the polymerization product thus obtained can have good transparency and can be in the form of a uniform and smooth paste or grease. Moreover, these oil components play a role as a diluent When the polymerization product is synthesized, and also enable the polymerization to proceed while retaining satisfactory three-dimensional crosslinked structure during the addition polymerization.

The addition polymerization should be carried out in the presence of an organometallic catalyst soluble to an organic solvent, such as a platinum compound as exemplified by chloroplatinate, alcohol-modified chloroplatinate and a chloroplatinate-vinylsiloxane complex, a palladium compound or a rhodium compound, at room temperature or under conditions of heating at about 50 to 150° C.

Of the above catalysts, preferred are chloroplatinate, the platinum compounds as exemplified by Pt(PPh$_3$) used in hydrosilylation as described in U.S. Pat. Nos. 3,159,601, 3,159,662 and 3,775,452 etc. Particularly preferred are a complex of vinylsiloxane with any of the platinum compounds described in the above U. S. Patents, and also the complex having been modified with alcohol, the chloroplatinic acid described in Japanese Patent Publication (KOKOKU) No. 9969/1958, and a complex of vinylsiloxane with chloroplatinic acid.

These catalysts may be used in the so-called catalytic amount. These are usually used in the form of a solution of an organic solvent. Such an organic solvent includes aliphatic alcohols such as methanol, ethanol, 2propanol, and butanol; aromatic hydrocarbons such as benzene, toluene, and xylene; aliphatic or alicyclic hydrocarbons such as n-pentane, n-hexane and cyclohexane; and halogenated hydrocarbons such as dichloromethane. chloroform, carbon tetrachloride, trichloroethane, trichloroethylene, and hydrocarbon fluoride chloride: which are used according to the type of the catalyst used.

The addition polymerization may be carried out by, for example, mixing the organohydrogenpolysiloxane of (A), the organopolysiloxane of (8), and the saturated hydrocarbon oil of (C) or low-viscosity silicone oil or the mixed oil of the (C) and (D), in respectively given amounts, followed by further addition of a catalyst, and stirring the mixture at an appropriate temperature.

The component (1) polymerization product thus synthesized comprises is a polymer with three-dimensional crosslinked structure, which is insoluble to the saturated hydrocarbon oil of (C) but capable of being swelled by it. In the inside thereof, the above saturated hydrocarbon oil of (C), low-viscosity silicone oil of (D) or the mixture of the both is retained.

(II) Saturated Hydrocarbon Oil

The oily paste composition of this invention comprises the component (II). saturated hydrocarbon oil, in addition to the component (I).

This component (II), saturated hydrocarbon oil, penetrates into the inside of the three-dimensional crosslinked structure of the component (I) polymerization product to swell the component (I). The uniform and smooth oily paste composition having good transparency can be thus obtained.

As such a saturated hydrocarbon oil, the saturated hydrocarbon oil of (C) that can be used when the above component (I) polymerization product is synthesized can be used.

Preparation of Oily Paste Composition

The oily paste composition of this invention is prepared, for example, by kneading 100 parts by weight of the component (I) polymerization product, together with from 10 to 1,000 parts by weight, preferably from 20 to 500 parts by weight, and most preferably from 100 to 500 parts by weight, of the component (II) saturated hydrocarbon oil under application of shearing force. Use of the component (II) in an amount less than 10 parts by weight can not bring about any uniform pasty form, and use thereof in an amount more than 1,000 parts by weight can give no composition having sufficient thickening properties, or can not bring about good pasty or greasy form.

This kneading must be carried out under application of shearing force. The kneading under application of shearing force makes it ready for the polymerization product to be uniformly swelled with the (II) saturated hydrocarbon oil. In other words, the kneading under application of shearing force makes it possible to achieve uniformity of the component (I) polymerization product and the component (II) saturated hydrocarbon oil, so that the pasty or greasy composition which is relatively highly viscous, uniform, and smooth in appearance can be readily obtained even though it is mainly composed of the saturated hydrocarbon oil.

No or insufficient application of the shearing force may result in a state in which the component (I) polymerization product and the component (II) saturated hydrocarbon oil remain separate, so that the resulting composition becomes non-uniform, has a low viscosity in itself, and can not be endowed with sufficient thickening properties. Since an insufficiently swelled polymerization product remains in the composition, the resulting composition becomes rough to touch and not smooth in appearance.

Apparatus that can be used to apply the shearing force include a three-roll mill, a two-roll mill, a colloid mill, a Gaulin homogenizer, etc. Of these, it is preferred to use a three-roll mill.

Oily Paste Composition

The oily paste composition of this invention, thus obtained, is a pasty or greasy composition which is smooth to touch and free from stickiness and yet has excellent transparency because of its components swelled and made uniform, even though it is mainly composed of the saturated hydrocarbon oil.

This composition can be widely used as it is or as a compounding material. More specifically, because of its excellent safety and feeling of lightness, it is suitable for cosmetic, medical or the like purpose. Since it has also a good transparency, it gives no limitation on use of any pigment for cosmetics. In particular, use of a highly volatile material as the saturated hydrocarbon oil can more improve the thickening properties of the resulting composition, so that an oily paste composition with a very component can be obtained, which composition is very useful as a material for cosmetics or medical supplies.

Because of good spreadability of this composition, a very good feeling in use can also be enjoyed when the composition is used as a base material of polishing materials for automobiles or furniture.

EXAMPLES

This invention will be described below in greater detail by way of Examples. These Examples, however, by no means limit this invention, viscosity set out in Examples refers to the value at 2S° C. The viscosity has measured according to JIS K2220.

EXAMPLE 1

In a planetary mixer with an internal volume of about 5 lit., 900 g of trimethylsilyl-terminated dimethyl-hydrogenpolysiloxane (average molecular weight: 2,280; Si—H: 3.1 mol %), 396 g of dimethylvinylsilyl-terminated dimethylpolysiloxane (average molecular weight: 930; vinyl group content: 7.7 mol %) and 864 g of dimethylpolysiloxane (viscosity: 6 cSt) were mixed with stirring. In the resulting mixed solution, 0.5 g of an 2% chloroplatinate solution in isopropanol was added, and stirring was continued at 70 to 80° C. for 2 hours. A white and soft powder was obtained as the polymerization product.

After 100 parts by weight of this polymerization product and 400 parts by weight of "Isopar G" (boiling temperature range: 158 to 177C.; product by Exxson Chemical K.K.) were dispersion mixed, the resulting mixture was thoroughly kneaded under application of shearing force using a three-roll mill to make the polymerization product swell. An oily paste composition with a viscosity of 17,000 cP was obtained, which had a colorless and transparent appearance.

For comparison, a mixture comprising 100 parts by weight of the above polymerization product and 400 parts by weight of "Isopar G" was stirred at room temperature for 2 hours, using a planetary mixer in place of the three-roll mill. However, the polymerization product was not sufficiently swelled, causing separation of the mixture into two layers. There was obtained no pasty composition which is uniform and soft to touch.

Thus, the application of sufficient shearing force, using the three-roll mill, made it possible to achieve uniform swelling of the polymerization product with the saturated hydrocarbon oil, resulting in a pasty composition with high thickening properties and smoothness to touch. Without application of shearing force, such a pasty composition was not obtainable.

The procedure of Example 1 was repeated to obtain a polymerization product, except that the materials charged in the planetary mixer were replaced with 1,400 g of trimethylsilyl-terminated dimethylhydrogen-polysiloxane (average molecular weight: 2,280 ; Si—H: 3.1 mol %)' 616 g of dimethylvinylsilyl-terminated dimethylpolysiloxane (average molecular weight: 930; vinyl group content: 7.7 mol %) and 1.0 g of a 2 % chloroplatinate solution in isopropanol, and the low-viscosity polysiloxane was not charged.

In the same manner as Example 1, 100 parts by weight of this polymerization product and 400 parts by weight of "Isopar G" were kneaded under application of shearing force to obtain an oily paste composition.

This composition, however, had a cloudy appearance and had a viscosity of 2,000 cP.

The results shows that absence of the low-viscosity dimethylpolysiloxane (viscosity: 6 cSt) results in a cloudy appearance and poor thickening properties.

EXAMPLE 2

The procedure of Example 1 was repeated to obtain a polymerization product, except that the charged materials were replaced with 320 g of trimethylsilyl-terminated dimethylhydrogenpolysiloxane (average molecular weight: 2,870; Si—H: 2.6 mol %), 616 g of dimethylvinylsilyl-terminated dimethylpolysiloxane (average molecular weight: 5,000; vinyl group content: 1.5 mol %), 936 g of a saturated hydrocarbon oil (boiling temperature range: 206 to 257° C.; "Isozole 400", product by Nippon Petrochemical Co., Ltd.) and 0.5 of a 2 % chloroplatinic acid solution in isopropanol.

In the same manner as in Example 1, an oily paste composition as prepared, except that 100 parts by weight of the above polymerization product and 30 parts by weight of "Isozole 400" mentioned above were mixed. This oily paste composition had a colorless transparent appearance, and had a viscosity of 18,000 cp.

EXAMPLE 3

The procedure of Example 1 was repeated to obtain a polymerization product, except that the charged materials terminated dimethylpolysiloxane (average molecular weight: 2,280: Si—H: 3.1 mol %), 786 g of trimethylsilyl-terminated dimethylvinylpolysiloxane (average molecular weight: 10,800; vinyl group content: 0.7 mol %), 1,404 g of dimethylpolysiloxane (viscosity: 6 cSt), and 0.5 g of a 2 % chloroplatinic acid solution in isopropanol.

In the same manner as in Example 1, an oily paste composition was prepared, except that 100 parts by weight of the above polymerization product and 300 parts by weight of "IP Solvent 1620" (boiling temperature range: 166 to 202° C.; product by ldemitsu petrochemical Go., L&d.) were mixed.

This oily paste composition had a colorless and transparent was greasy, and had an unworked consistency of 390 and a worked consistency of 395. Transmittance of visible light was also measured to find that the composition showed a transmittance of 90 % or more over a wavelength region of from 340 to 700 nm.

EXAMPLE 4

The procedure of Example 1 was repeated to obtain a polymerization product, except that the charged materials were replaced with 140 g of trimethylsilyl-terminated dimethylhydrogenpolysiloxane (average molecular weight: 2,280; Si—H: 3.1 mol %), 340 g of dimethylvinylsilyl-terminated dimethylpolysiloxane (average molecular weight: 5,000; vinyl group content: 1.5 mol %), 1,918 g of octamethylcyclotetrasiloxane and 0.3 g of a 2 % chloroplatinic acid solution in isopropanol.

In the same manner as in Example 1, an oily paste composition was prepared, except that 100 parts by weight of this polymerization product, 100 parts by weight of a saturated hydrocarbon oil "Marukazole R" (boiling temperature range: 178.5 to 181.0° C.; product by Maruzen Petrochemical Co., Ltd.) and 200 parts by weight of "Isopar H" (boiling temperature range: 174 to 189° C.; product by Exxson Chemical K.K.) were mixed.

This composition had a colorless and transparent appearance, and had a viscosity of 16,000 cP. This showed a heat loss of 95 % at 150° C. after 30 minutes, indicating that a stable oily paste composition can be obtained using a very small amount& of a silicone polymer.

EXAMPLE 5

The procedure of Example 1 was repeated to obtain a polymerization product, except that the charged materials were replaced with 200 g of trimethylsilyl-terminated dimethylhydrogenpolysiloxane (average molecular weight: 2,280: Si—H: 3.1 mol %), 485 g of dimethylvinylsilyl-terminated dimethylpolysiloxane (average molecular weight: 5,000; vinyl group content: 1.5 mol %), 514 g of a saturated hydrocarbon oil (boiling temperature range: 207 to 257 ° C.; "Isopar M", product by Exxon Chemical Japan Ltd.), and 514 g of phenyltristrimethylsiloxysilane (viscosity: 4.0 cSt) were mixed, 0.5 g of a 2 % chloroplatinic acid solution in isopropanol.

In the same manner as in Example 1, an oily paste composition was prepared except that 100 parts by weight of the above polymerization product and 300 parts by eight of "Isopar M" mentioned above were mixed. This oily paste composition had a smooth appearance with a rich spreadability, and had a viscosity of 50,000 cP.

EXAMPLE 6

The procedure of Example 1 was repeated to obtain a polymerization product, except that the charged materials were replaced with 320 g of dimethylhydrogensilyl-terminated dimethylpolysiloxane (average molecular weight: 2,870; Si—H: 2.5 mol %), 616 g of trimethylsilyl-terminated dimethylvinylpolysiloxane (average molecular weight: 5,000: vinyl group content: 1.5 mol %) and 1,405 g of methyltris(trimethylsiloxy)silane (viscosity: 1.6 cBt). and 0.5 g of a 2 % chloroplatinic acid solution in isopropanol.

In the same manner as in Example 1, an oily paste composition was prepared, except that 100 parts by weight of this polymerization product and 300 parts by weight of a saturated hydrocarbon oil ("Isozole 300"; boiling temperature range: 170 to 189° C. product by Nippon Petrochemical Co., Ltd.) were mixed.

This composition had a colorless and transparent appearance, and had a viscosity of 150,000 cP.

EXAMPLE 7

The procedure of Example 1 was repeated to obtain a polymerization product, except that the charged materials were replaced with 30 g of trimethylsilyl-terminated dimethylhydrogenpolysiloxane (average molecular weight: 11,200; Si—H content: 18.4 mol %), 1,140 g of dimethylvinylsilyl-terminated dimethylpolysiloxane (average molecular weight: 14,200; vinyl group content: 0.52 mol %), 585g of a saturated hydrocarbon oil (boiling temperature range: 213 to 262° C.; "IP Solvent 2028": product by Idemitsu Petrochemical Co., Ltd.) and 585 g of octamethyltrisiloxane (viscosity: 1.0 cSt), 0.5 g of a 2 % chloroplatinic acid solution in isopropanol.

In the same manner as in Example 1, an oily paste composition was prepared, except that 100 parts by weight of the above polymerization product and 200 parts by weight of "IP Solvent 2028" mentioned above were mIxed. This composition had a colorless transparent appearance, and had a viscosity of 20.000 cp.

We claim:

1. An oily paste composition comprising:
   (I) 100 parts by weight of a polymerization products obtained by addition polymerization of an organohydrogenpolysiloxane of (A) given below and an organopolysiloxane of (B) given below in the presence of at least one member selected from the group consisting of a saturated hydrocarbon oil of (C) given below and a low-viscosity silicone oil of (D) given below: and
   (II) from 10 to 1,000 parts by weight of a saturated hydrocarbon oil of (C) given below.
   (A): An organohydrogenpolysiloxane containing in its molecule not less than 1.5 silicon-bonded hydrogen atoms on average.
   (B): An organopolysiloxane containing in its molecule not less than 1.5 silicon-bonded aliphatic unsaturated groups on average.
   (C): A saturated hydrocarbon oil with a boiling temperature range of from 70 to 360° C.
   (D): A low-viscosity silicone oil with a viscosity of not more than 100 cSt at 25° C. wherein the (a) organohydrogenpolysiloxane and (B) organopolysiloxane are used in such a proportion that the molar ratio of the silicon-bonded hydrogen atoms possessed by (A) to the silicon-bonded aliphatic unsaturated groups possessed by (B) ranges from 1/3 to 3/1.

2. The oily paste composition of claim 1, wherein in said (I) polymerization product at least one of the (C) saturated hydrocarbon oil and (D) low-viscosity silicone oil is used in an amount of from 10 to 1,000 parts by weight based on 100 parts by total weight of the (A) organohydrogenpolysiloxane and the (B) organopolysiloxane.

3. The oily paste composition of claim 1, wherein said (A) organohydrogenpolysiloxane contains the silicon-bonded hydrogen atoms in a proportion of from 0.5 to 20 mol % based on the total of the silicon-bonded hydrogen atoms and organic groups.

4. The oily paste composition of claim 1, wherein in said (B) organopolysiloxane the aliphatic unsaturated groups comprise 0.6 to 20 mol % of the silicon-bonded organic groups.

5. The oily paste composition of claim 1, therein the component (II) saturated hydrocarbon oil is mixed in an amount of from 100 to 500 parts by weight based on 100 parts by weight of the component (I) polymerization product.

6. The oily paste composition of claim 1, which is obtained by kneading the component (I) polymerization product and the component (II) saturated hydrocarbon oil under application of shearing force.

7. A cosmetic material comprising the oily paste composition of claim 1.

8. A polishing material comprising the oily paste composition of claim 1.

* * * * *